United States Patent [19]

Devlin

[11] 3,951,748

[45] Apr. 20, 1976

[54] SENSITIZED MATRIX FOR DETECTION OF DISEASE

[75] Inventor: Robert Francis Devlin, Keene, Tex.

[73] Assignee: Medical Products, Inc., Houston, Tex.

[22] Filed: Nov. 11, 1974

[21] Appl. No.: 522,722

[52] U.S. Cl. .......................... 195/103.5 R; 424/12; 23/230 B
[51] Int. Cl.² ......................................... C12K 1/04
[58] Field of Search .............. 195/103.5 R, 99, 100, 195/101, 102; 424/12; 23/230 B

[56] References Cited
UNITED STATES PATENTS 3,791,932  2/1974  Schuurs et al. .............. 195/103.5 R

OTHER PUBLICATIONS

Silman et al., "Water–Insoluble Derivatives of Enzymes, Antigens, and Antibodies", Annual Review of Biochemistry, Vol. 35, pt. II, 1966, pp. 873–880.

Primary Examiner—A. Louis Monacell
Assistant Examiner—C. A. Fan
Attorney, Agent, or Firm—Pravel & Wilson

[57] ABSTRACT

A specific sensitized matrix for diagnosing both infectious and non-infectious disease is disclosed comprised of an insoluble, inert, pliable and wettable matrix having a network of pores, and a protein polymer network immobilized in the network of pores formed of protein carrier molecules, specific antigens or antibodies, and a coupling agent coupling the protein carrier molecules together and the antigen or antibody to the protein carrier molecules. A variety of matrix materials, protein carrier molecules, specific antigens or antibodies and coupling agents can be used. Methods of preparing the sensitized matrix and diagnostic test procedures utilizing the sensitized matrix for detecting disease are also disclosed.

25 Claims, 2 Drawing Figures

SENSITIZED MATRIX FOR DETECTION OF DISEASE

BACKGROUND OF THE INVENTION

There are several types of test systems currently used for the serological detection of certain infectious diseases. These include the following:
1. Latex particle agglutination (LPA).
2. Charcoal particle agglutination (CPA).
3. Hemaagglutination (HA).
4. Complement Fixation (CF).
5. Fluorescent Antibody (FA).
6. Counter-electrophoresis (CEP).
7. Double diffusion (DD).
8. Radioimmunoassay (RIA).
9. Peroxidase tagged antibody (PTA).

Most of these tests are limited by one or more or all of the following limitations: (1) sensitivity; (2) complexity of the test procedure; and requirements for unstable reagents; (3) the carrier itself is unstable; (4) reagents may be dangerous; (5) the requirement for expensive equipment and thus experience in their operation; and (6) lack of specificity of the specific antigen used.

The sensitivity and the utility of or ease of running a serological test is of major importance as each characteristic may be cross-dependent in some ways and may be mutually independent in other ways. Usually, as the system's sensitivity becomes greater, the more complex it is and thus the requirement for more sophisticated equipment. Sensitivity of serological tests may be looked at at levels. These include a moderate range of sensitivity, which include DD, CPA, LPA and CE; mid-range which include HA, CF, FA and PTA, and ultra-low which includes RIA. Thus it is noted that there are several test systems that fit into the mid-range of sensitivity, but these are severely limited by unstable reagents and/or the requirement for use of complex equipment. Advantageously, however, the present invention can be used in the mid-range area of sensitivity, however it is not limited to this level, but can be used in the lower sensitivity range.

For a review of the development and evolution of immunological methods and their use as diagnostic laboratory tools, reference is made to "Immunology As a Laboratory Tool" by Frans Peetoom, M.D., PhD, appearing in the American Journal of Medical Technology, Volume 37, No. 12, Dec. 1971, pp. 455-469.

SUMMARY

The present invention relates to a sensitized matrix which can readily and easily be used in serological and immunological tests for detection of both infectious and non-infectious diseases and which comprises an insoluble, wettable and preferably a pliable and inert matrix under conditions of use and having an extensive network of pores in which a network of protein carrier molecules bound together and a specific antibody or antigen bound to the protein carrier molecules by a coupling agent is immobilized, and to methods of preparation of the sensitized matrix and diagnostic test procedures for detecting disease with the sensitized matrices. Advantageously the sensitized matrix of the present invention is more sensitive than the more commonly used techniques at the present time, such as double diffusion, charcoal particles and latex particle agglutination, counter electrophoresis, complement fixation and fluorescent antibody. Also, the reagent is more stable than latex and/or charcoal particle agglutination where substantial elution can occur, and does not require for normal use complex or dangerous chemicals, i.e., radioactive compounds which may require special handling equipment, which is expensive or complicated, such as gamma and scintillation counters, fluorescent microscopes, fluorometers, spectophotometers although these instruments can be used to increase sensitivity and to obtain qualitative data.

A variety of matrix materials can be used, for example, polyurethane foam, polystyrene latex particles, expanded polystyrene foam, cellulose fiber filter papers of various porosities and thicknesses, cellulose nitrate membranes, cellulose acetate membranes, controlled pore porcelain, controlled pore glass, foam sponges made of other types of polymers, and including natural sponges. The matrix should be wettable, insoluble and inert under conditions of use, and preferably pliable, and have a substantial amount of pores, for example, at least 50% by volume, should be able to withstand freezing at low temperatures (−70° C.) and capable of being freeze dried without adverse effects on the matrix. These materials are readily available and, accordingly, no detailed description of their preparation is deemed necessary or given.

Almost any protein molecules can be used as the protein carrier molecules, for example, bovine serum albumin, bovine gamma globulin, any fraction of bovine serum, fetal calf serum, neo-natal calf serum, serum albumin from any animal species other than human, serum proteins from any animal species other than human, limpet crab hemocyanin, and the like.

The sensitized matrix is used in serological and/or immunological tests for the detection of certain infectious and non-infectious disease states by the use of specific antigens or antibodies derived from the causative organism. The infectious diseases include those caused by parasites, bacteria, fungi, viruses; non-infectious diseases include various allergies; and disease states include cancer, rheumatoid arthritis, and the like, a representative list of which are included in the description of the presently preferred embodiments.

Any combination of a particular matrix, having one carrier protein molecules bound together to which one specific antigens or antibodies is bonded or coupled and immobilized in the pores of the matrix constitutes a specific sensitized matrix according to the present invention for use in detection of disease.

The specific sensitized matrix is prepared by saturating at least a portion and preferably the entire matrix with a buffered mixture of protein carrier molecules having a pH of about 4 to about 7, a specific immunological reactant (antigen or antibodies), and a coupling agent capable of bonding the protein carrier molecules together and antigens or antibodies to the protein carrier molecules in situ in the network of pores of the matrix. The saturated matrix is then incubated so as to form a network of coupled protein carrier molecules and antigen or antibodies which are immobilized within the pores of the matrix.

The method of diagnosing a specific disease comprises incubating the sensitized matrix having antigen or antibodies, as the case may be, known to be specific to the disease for which the patient is being tested, with the blood serum of the patient so as to bind the patient's blood serum to the sensitized matrix. The sensitized matrix is then washed of unbound blood serum and then contacted with a reagent capable of catalyzing a measurable reaction so as to bind the reagent to any corresponding opposite reactant of the antigen or antibodies from the patient's serum bound to the specific sensitized protein carrier molecules. Unbound reagent is then removed by washing, and the sensitized matrix is then subjected to a suitable substrate so as to produce a measurable catalytic reaction for measurement of the reagent and hence a determination of the presence or absence of the disease being tested for in the patient.

The reagent may be an enzyme labeled, fluorescein isothiocyanate labeled, or radioisotope labeled IgG fractions of goat, rabbit or horse antiserums to human IgG and/or IgA, and/or IgM. The reaction can be read visually when using an enzyme labeled material, the fluoroescence can be measured when using fluorescein isothiocyanate labeled material, and radioactivity can be measured when using the radioisotope labeled material. Additional details, examples and the like are given in the detailed description of the preferred embodiments.

Accordingly, it is an object of the present invention to provide a sensitized matrix which is highly sensitive and which can be used readily and easily for specific diagnosis of a wide variety of diseases, both infectious and non-infectious.

A further object of the present invention is the provision of methods of preparing a sensitized matrix which is highly sensitive and which can be used readily and easily for specific detection of a wide variety of diseases, both infectious and non-infectious.

A further object of the present invention is the provision of a relatively simple yet highly effective and sensitive diagnostic test for the detection of specific disease states, both infectious and non-infectious.

A further object of the present invention is the provision of a specific sensitized matrix, its method of preparation and a diagnostic test utilizing the specific sensitized matrix for the detection of infectious gonorrhea.

A further object of the present invention is the provision of a specific sensitized matrix comprised of a relatively inert, insoluble, wettable matrix under the conditions of use, having a porous structure in which polymers of protein molecule carriers and antigens or antibodies are physically trapped for use in diagnostic tests for specific diseases.

A further object of the present invention is the provision of such a specific sensitized matrix, its method of preparation, and use in diagnostic tests, which does not require centrifugation steps, where the reagent is stable and elution does not occur, which has a high degree of specificity, in which the reagent is more sensitive than in the currently available techniques and which does not require the use of complex or dangerous chemicals or expensive or complicated equipment in normal use which, however, can be used to increase sensitivity if desired.

Other and further objects, features and advantages of the invention will appear from the abstract of the disclosure, the background of the invention, this summary, the drawing, the description of presently preferred embodiments, and the claims.

DESCRIPTION OF THE PREFERRED EMBODIMENT

Figures 1, 2:
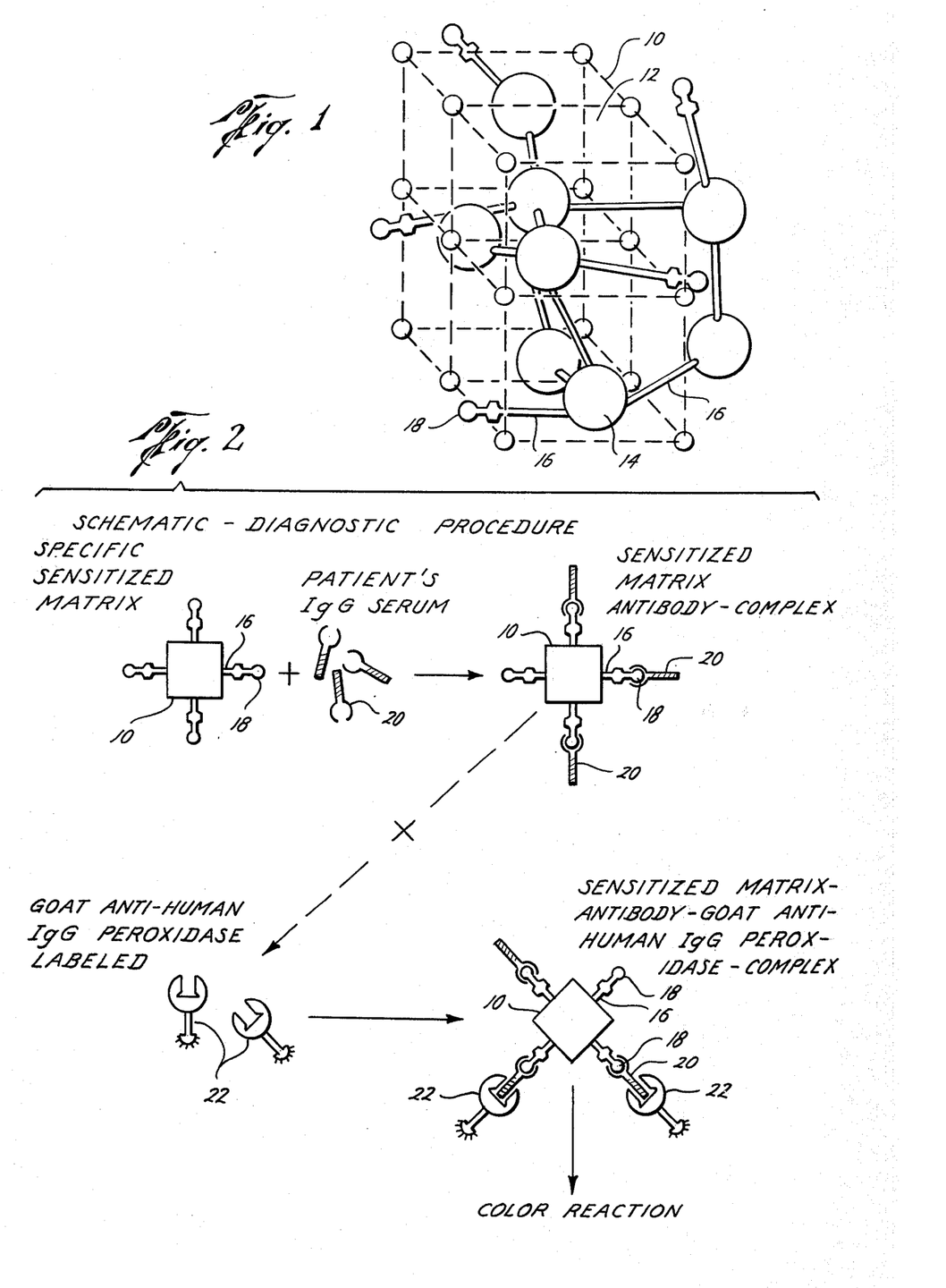
FIG. 1 illustrates a magnified matrix having an extensive network of pores in which protein carrier molecules, coupling agent and specific antibodies or antigens are chemically bonded or coupled in the form of a network immobilized or trapped in the network of pores.
FIG. 2 is a schematic diagram illustrating a diagnostic procedure using the specific sensitized matrix of FIG. 1.

Referring to the drawing, a specific sensitized matrix according to the invention is illustrated, greatly enlarged, which includes the matrix 10 having an extensive network of pores 12 in which are disposed the protein carrier molecules 14 which are coupled together by the coupling agents 16 which also couple the antigens or antibodies 18 to the protein carrier molecules 14. The polymerized protein carrier molecules, coupling agent and specific antigens and specific antibodies form a network which is immmobilized or trapped within the network of pores 12 in the matrix 10.

The matrix may be formed of a wide variety of materials, the requirement being that the material is insoluble and preferably inert with respect to the various reagents used in forming the sensitized matrix and in using it in diagnostic tests, that it be wettable by the liquids used in its preparation and in diagnostic testing, and preferably that it be pliable to the extent that it can be gently massaged or pressed during its preparation so that at least a portion of it, and preferably all of it, can be completely saturated. It should have an extensive network of pores, at least 50% by volume of pore space, and preferaby 85 to 95% by volume. Among materials which are suitable for use as matrix materials are polyurethane foam, polystyrene latex particles, expanded polystyrene foam, cellulose fiber filter papers of porosities from 0 to 50% by volume, and of various thicknesses, cellulose nitrate membranes, cellulose acetate membranes, controlled pore procelain, foam sponges made of other types of polymers and natural sponges. It also should be able to withstand freezing at low temperatures (−70° C.) and capable of being freeze dried without adverse effect on the matrix. It can be in a variety of physical shapes or forms, such as 1 cm. by 1 cm. cylinders, cubes, etc.

The coupling agent used should be able to couple the functional group involved. Glutaraldehyde is an important chemical coupling agent for the coupling of certain antigens to other proteins such as BSA. There are many other multi-functional reagents which can be substituted in order to build the polymers within the matrix. These include cyanogen bromide, chloro-s-triazine, 4,4-difluoro-3, 3-dinitrophenylsulfone, ethylchloroformate, diethyl malonimidate dihydrochloride, ethylene maleic anhydride, N,N-dicyclohexyl carbodiimide, dinitrofluorobenzene, tributylamine, sodium periodate (periodic acid), bis-diazotized benzidine, to name a few.

If desired, a combination of coupling agents can be used; for example glutaraldehyde and tributylamine, glutaraldehyde and ethyl chloroformate, water soluble carbodiamides for coupling carbohydrates to polymerized BSA molecules, as well as other combinations.

For a discussion of various coupling and polymerizing agents, reference is made to the following publications: Coupling of Enzymes to Proteins With Glutaraldehyde, Immunochemistry, Pargamon Press, 1969, Volume 6, pages 43–52; The Cross-Linking of Proteins With Glutaraldehyde and its Use for the Preparation of Immunoadsorbents, Immunochemistry, Pargamon Press, 1969, Volume 6, pages 53–66; Chemical Coupling of Peptides and Proteins to Polysaccharides by Means of Cyanogen Halides Nature, Volume 214, June 24, 1967, pages 1302–1304, The Use of Ethylene Maleic Anhydride for the Preparation of Versatile Immunoadsorbents, Immunochemistry, Pargamon Press, 1971, Volume 8, pages 887–900; Bifunctional Imidoesters as Cross-Linking Reagents, Biochemical and Biophysical Research Communication, Volume 23, No. 5, 1966, pages 730,739; Sensitization of Erythrocytes With Lipopolysaccharides Using Glutaraldehyde As a Coupling Agent, Immunology, Aug. 1971, Volume 21, pages 311–312; Reaction of Proteins With Glutaraldehyde, Archives of Biochemistry and Biophysics, 126, 16–26, July-Sept. 1968; and U.S. Pat. No. 3,645,852, Method of Binding Water Soluble Proteins and Water Soluble Peptides to Water Insoluble Polymers Using Cyanogen Halide.

The degree and speed of the polymerization of the specific antigen or antibody to the protein carrier molecules is directly related to the concentration of the coupling agent. Thus if larger polymers are desired to fill a sponge with larger pores, higher concentrations of both coupling agent and the protein carrier molecules should be used. For example, from about 0.05% to about 6% by weight of the coupling agent may be used.

It is important that the coupling reaction take place at an acid pH, i.e., about 4.0–7.0, with an optimal pH of 4.9. While a variety of buffer systems can be used, such as phosphate and the like, an acetate buffer is preferred because it is a better functioning buffer at a pH of about 4.9.

Another influencing factor involved in coupling is the stablility of the specific antigen or antibody in question. These may be extremely sensitive to denaturation and a lower concentration of coupling agent and a longer coupling time is advantageous.

A wide variety of disease states can be diagnosed with the sensitized matrix and the antigen derived from the causative organism or other specific antigens and antibodies can be used in the diagnosis of disease states with respect to the causative organism. No attempt is made to list all of the disease states, and hence specific antigens or antibodies, but the following Table I lists representative diseases, causative organisms, antigens and antibodies within the scope of the invention.

TABLE I

Disease States and Antigen Derived From the Causitive Organism or Other Specific Antigens Used in the Diagnosis of Certain Disease States 1. Infectious Diseases.
   A. Parasites.

| Disease | Organism | Antigen |
|---|---|---|
| Amoebiasis | Entamobia histolytica | Organism sonicate of strain HK-9 |
| Toxoplasmosis | Toxoplasma gondii | Whole organism or there sonicate derived from tissue culture or mouse peritoneal fluid |
| Chagas | Typanosoma cruzi | Organism sonicate derived from tissue culture |
| Schistosomiasis | Schistosoma haematobium Schistosoma japonicum Schistosoma mansoni | Culture filtrates |

B. Bacteria.

| Disease | Organism | Antigen |
|---|---|---|
| Infectious meningitis | Neisseria meningitidis | Capsular polysaccharide |
| Gonorrhea | Neisseria gonorrheae | Pili isolated from the bacterial cells |
| Typhoid fever | Salmonella typhi | Bacterial cells or their extracts |
| Pneumonia | Diplococcus pneumoniae | Capsular polysaccharide |

C. Fungi.

| Disease | Organism | Antigen |
|---|---|---|
| Histoplasmosis | Histoplasma capsulatum | Culture filtrate |
| Blastomycosis | Blastomyces dermatitidis | Culture filtrate |
| Coccidioidomycosis | Coccidioides immitis | Culture filtrate |

D. Viruses.

| Disease | Organism | Antigen |
|---|---|---|
| Rubella | Rubella virus | Virus particles |
| Measles | Measles virus | Virus particles |
| Rabies | Rabies virus | Virus particles |

2. Allergies.

| | | |
|---|---|---|
| | Ragweed pollen | Pollen extract |
| | Tomatoes | Tomato extract |
| | Bermuda grass seed | Seed extract |
| | Cat dander | Fur extract |
| | House dirt | Dust extract |

3. Disease States.

| Disease | Organism | Antigen |
|---|---|---|
| Lupus erythermatosis | | DNA molecules RNA molecules |
| Rheumatoid arthritis | | Human IgG |
| Colon cancer | | CEA antigen |
| Hepatoma | | Alpha-1-feto protein |

METHODS OF PREPARING THE SENSITIZED MATRIX

In preparing the specific sensitized matrix, a buffered solution of antigens or antibodies, protein carrier molecules, and a coupling agent are combined and mixed together and then added to one or more matrices in one or more containers such as a cylinder, glass tubing and the like, in which event the matrices may be cylinders 1 cm. by 1 cm. Preferably the matrices are massaged, such as with a small glass rod, in order to completely saturate the matrices with this reaction mixture. It is important that the coupling reaction for polymerization take place at an acid pH, about 4.0–7.0, with the optimal pH at 4.9. For this purpose, a suitable buffer, such as an acetate or phosphate buffer is used, the acetate buffer being preferred because it is a better functioning buffer at a pH of about 4.9.

The containers are then closed, such as with stoppers, and the stopped tubes containing the saturated matrices are stored and incubated for a time period sufficient to polymerize or couple the protein carrier molecules and antigens or antibodies. Preferably the storage and incubation is at 4° C. for a period of about 24 hours.

The degree and speed of polymerization of the specific antigen or antibody to the protein carrier molecules is directly related to the concentration of the coupling agent. Thus, if larger polymers are desired to fill a matrix with larger pores, then higher concentrations of both the coupling agent and the protein carrier molecules are used. For example, the coupling agent can vary from about 0.05% to about 6.0% by weight. Another influencing factor is the stability of the specific antigen or antibody being used. These may be extremely sensitive to denaturation and the lower concentration of the coupling agent and a longer coupling time wll be advantageous. It is also important to use a coupling agent which will couple the functional groups of the antigens or antibodies being coupled with the protein carrier molecules. For example, glutaraldehyde is an important chemical coupling agent for the coupling of many antigens and antibodies to other proteins, such as protein carrier molecules as BSA. Glutaraldehyde, however, will not couple all proteins, in which event other coupling compounds as mentioned previously should be used.

After incubation, the matrices are removed from the container and washed of unreacted protein, preferably with an acetate buffer in which the matrices are allowed to sit for approximately 10 minutes.

It is important that any residual reactive groups of the coupling agent are blocked. For example, in using glutaraldehyde, the residual reactive aldehyde groups are blocked by combining with the amino groups found on the glycine molecule, which has the simplest chemical formula of the amino acids and is preferred; however, any one of the amino acids can be used. Preferably the amino acid should be in an acetate buffered solution, for example glycine 0.1 in acetate buffer.

The matrices are allowed to sit in the blocking reagent solution for a sufficient length of time to combine the residual reactive groups and permitting the matrices to sit in the solution for 30 minutes with occasional agitation is sufficient. The matrices are then washed repetitively, for example 4 times, by gentle agitation in a suitable buffer, for example 30 ml. of phosphate buffer.

After the repetitive washing, the specific sensitized matrix is ready to use in the diagnostic procedure, or it can be stored at 4° C. in a small amount of a phosphate buffer for future use.

Other methods for the preparation of the sensitized matrix can be used which are only limited by the type of matrix material. The following are two alternate methods which can be employed for the manufacture of the specific sensitized matrix on a large scale. These include the dialysis method in which a matrix, protein carrier molecule solution, antigen or antibody solution and buffer are placed within a dialysis tubing of suitable size. The concentration of reactants is the same, the tubing is tied securely and suspended in a solution of buffer and coupling agent, and the reaction is allowed to incubate for about 24 hours at 4° C. After this period of time, the matrices are removed, washed, residual reactive groups are blocked, and washed again, all as previously described.

A second method includes what might be termed a solid sheet method which is the same as previously outlined except that the matrix is prepared in large sheets with the volume and concentration relationship of reactants being the same as in the other methods. The matrix sheets are treated the same as the cylinders except that after the blocking reaction and washing, the sheet is maintained flat, uniform and freeze dried. After freeze-drying, the appropriate size and shape of sensitized matrix is prepared by either cutting the matrix with a cork borer, dye cutter, paper cutter or other cutting means.

The following are examples of specific sensitized matrices and their methods of manufacture according to the invention. As indicated above, however, a wide variety of specific sensitized matrices are within the scope of the invention and may be made by a variety of methods according to the invention, so that the following examples must be deemed as being representative of the present invention.

EXAMPLE 1.

In this example, 0.10 ml. glutaraldehyde solution, 0.1 ml. *Entamoeba histolytica* antigen and 2.5 ml. BSA solution were mixed and added to a suitable cylinder, such as a glass tubing or a 2.5 cc. syringe, containing four 1 cm. × 1 cm. polyurethane foam matrices in the shape of cylinders. The matrices were massaged with a small glass rod in order to completely saturate the matrices wih the reaction mixture, the tube was stoppered and stored at 4° C. and incubated for 24 hours.

After incubation, the matrices were removed from the cylinders and washed once with 20 ml. of acetate buffer by allowing the matrices to sit in the buffer for approximately 10 minutes. The matrices were then placed in a 20 ml. quantity of glycine solution and allowed to sit for 30 minutes with occasional agitation to block the residual reactive aldehyde groups by combining them with the amino groups found on the glycine molecule. The matrices were then washed four times by gentle agitation in 30 ml. phosphate buffer. After the fourth wash, the specific sensitized matrices were ready for use in the diagnostic procedure, or for storage at 4° C. in a small amount of phosphate buffer for future use.

EXAMPLE 2.

In this example, the matrix, before sensitization, is fastened to the bottom of a polystyrene tube by the use of an ethylene dichloride glue. After fixation to the tube, the tubes are allowed to aerate for several hours in order to remove any residual ethylene dichloride which will volatize.

The predetermined amount of buffer, albumin, antigen and glutaraldehyde, as set forth in Example 1, is pipetted into the bottom of the test tube. The matrix is massaged gently until all the liquid is taken up by the matrix. The tubes are incubated at 4° C. for 24 hours. After washing with acetate buffer, the matrices are allowed to set in 0.1M glycine for 30 minutes to block residual reactive groups and then washed with phosphate buffer. The matrix is now ready for use in the diagnostic test.

EXAMPLE 3.

In this example, the appropriate size matrix is fastened to the polystyrene stick by use of ethylene dichloride glue and aerated as in Example 2. The appropriate amount of buffer, albumin, antigen and glutaraldehyde, as set forth in Example 1, is pipetted into a tube, watch glass, spot plate or other suitable container and the matrix is filled with the solution by gently massaging the matrix in and up and down movement. Once the matrix is saturated, it is incubated and treated as in Example 2.

EXAMPLE 4.

In this example, a combination of chemical coupling agents was used and the matrix was sensitized with calf thymus DNA in order for the matrix to be used in a diagnostic test for Lupus Erythermatosis.

The matrix was senstiized by a slightly different manner than in Example 1. The BSA molecules were polymerized within the matrix as outlined in Example 1, except that no antigen was added to the BSA. The polymerization was allowed to proceed for 24 hours, after which excess glutaraldehyde was removed by washing with acetate buffer.

The DNA was then coupled to the polymerized BSA by the addition of a DNA-tributylamine mixture. After incubation for 2 hours, excess reagents were removed by washing the matrices with acetate buffer and blocking of any residual reactive groups with 0.1M glycine. The sensitized matrix was then ready to be used in the diagnostic test.

EXAMPLE 5.

In this example, the matrix was sensitized with antigen E (short ragweed pollen) in order to determine the allergic sensitivity of a patient to antigen E.

The BSA was polymerized in the matrix as outlined in Example 4, a solution of 20 mg. antigen E in 5 ml. acetate buffer pH 5.0, 0.02M and ethyl chlorformate (0.2 ml.) was added to the matrix. The reaction was allowed to continue for one hour and the matrix was washed with phosphate buffer. The sensitized matrix was then ready to be used in the diagnostic test.

SPECIFIC SENSITIZED MATRIX DIAGNOSTIC TESTS

In using a specific sensitized matrix in a diagnostic test, the matrix is incubated with the blood serum of a patient suspected of having the disease for which the specific sensitized matrix has been sensitized to detect. After the incubation period, the matrix is washed of unwanted protein from the serum. At this time, a reaction has occurred if the patient had the disease in question; however, whether or not a reaction has occurred cannot be determined at this point in the test procedure. In order to determine whether or not such a reaction has occurred, the matrix must be incubated with a tagging or indicator reagent or substance which can be read or which can catalyze a measurable endpoint reaction. These include an enzyme labeled anti-human IgG serum, a fluorescein isothiocyanate labeled anti-human IgG serum, and a radioisotope labeled serum. The results can be visually read in the case of the enzyme or fluorochrome labeled material. If quantative data is desired, the test can be read in a spectrophotometer in the case of the enzyme labeled material, a fluorometer in the case of the fluorochrome labeled material, or in a gamma or scintillation counter in the case of the radioactive isotope.

A diagnostic procedure utilizing a color reaction is graphically shown in FIG. 2, to which reference is now made. The patient's IgG serum 20 has reacted with the specific antigens 18. Tagging or labeling is accomplished by a tagging or indicator agent 22, here shown as goat anti-human IgG Peroxidase, and the results are indicated by the color reaction.

Among the tagging or indicator agents are goat anti-human IgG-Peroxidase, Fluorescein Isothiocynate (FITC), anti-human IgG-$I^{131}$ or IgG-$I^{125}$ labeled serum. Other electron donors or color reagents are set forth in the following tables:

TABLE II

| Emerald Green: | |
|---|---|
| 0.5 ml. | 10% acetic acid. |
| 3.4 ml. | 0.1M acetate buffer pH 4.6. |
| 0.01 ml. | O-Tolidine (25mg/ml). |
| 0.1 ml. | $H_2O_2$ (1%) |

This substrate color-reaction has the advantage that it reacts very rapidly and hence appears more sensitive. Most important, the color is very soluble and does not stay within the matrix but is eluted into the surrounding liquid. This is important when the tests are being read in a spectrophotometer.

TABLE III

| Lavender Color: | |
|---|---|
| 0.1 ml. | O-Tolidine (25 mg/ml). |
| 1.0 ml. | Guaiacol/Sucrose. |
| 2.0 ml. | 0.1 acetate buffer pH 6.0. |
| 0.1 ml. | $H_2O_2$ (1%). |

This color reaction is also very fast, but the reaction stays almost entirely within the sponge. Thus, the advantage of using this reaction mixture is that when reading the test visually, more color will be concentrated within the sponge allowing for a more objective reading.

Other electron donors or color reagents may be used. For example, guaiacol-sucrose solution (33 mM guaiacol in 0.25 M sucrose), benzedine, O-tolidine, pyrogallol, dimethyl-p-phenylenediamide, dianisidine. For additional compounds, which are electron donors for peroxidatic oxidations, and which are capable of forming oxidation dyes, reference is made to Enzyme Histochemistry 1962, M. S. Burstone, Academic Press.

The following examples illustrate diagnostic tests of the present invention and how they can be efficiently carried out. Again, these examples are representative.

EXAMPLE 6.

The reagents utilized in this example include (1) appropriate specific sensitized matrices, (2) the appropriate positive control serum, (3) the appropriate negative control serum, (4) goat anti-human IgG peroxidase labeled serum, (5) phosphate buffer 0.1 M, pH 7.4., (6) quaiacol-sucrose solution (33 mM quaiacol in 0.25 M sucrose), and (7) 1.0% hydrogen peroxide.

The matrices were placed in appropriate labeled tubes, and the known negative and positive control serum tubes were also labeled. To each tube, 1.0 ml. of the phosphate buffer solution was added and 0.1 ml. of the appropriate test serum, or its dilution. The tube was gently shaken and incubation at 37° C. for 30 minutes was permitted. Each matrix was washed with cold phosphate buffer solution by gently squirting it into each matrix tube (approximately 20 ml.), the tubes were gently rotated to assure thorough washing of the matrices, and the wash liquid discarded. This washing procedure was repeated an additional three times.

To each tube there was added 1.0 ml. phosphate buffer solution and 0.4 ml. of the anti-globulin (IgG) enzyme labeled serum, each tube was gently shaken and incubation at 37° C. for about 30 minutes was permitted. Each of the matrices was then washed with cold phosphate buffer solution by gently squirting it into each matrix tube (approximately 20 ml.) while gently rotating to assure thorough washing of the matrix, the washed liquid then being discarded by decantation. This washing was repeated an additional three times.

2.5 ml. phosphate buffer, 0.1 ml. of 1.0% hydrogen peroxide, and 1.5 ml. quaiacol-sucrose solution were added to separate appropriately labeled test tubes, the reaction mixture was thoroughly mixed, and the appropriate matrix was added to each tube. No shaking or mixing was necessary as the reaction took place within the matrix. A positive reaction was indicated by an orange-brown coloration of the test matrix as compared to the white matrix seen in the negative control tube. The sponge coloration reached maximum intensity in about 5 minutes at room temperature. Additionally, the reaction mixture reagents can be all mixed together in the appropriate concentration and pipetted at one time into the test tubes containing the reacted matrix. If this is done, the total volume of reagent can be reduced to 1.0 ml. and still the same intensity of reaction is obtained.

EXAMPLE 7.

In many cases involving an infectious disease process, it is advantageous for a physician to obtain information on the relative response that the patient has made to the infectious agent. The usual procedure is to perform a titration which in essence is accomplished by making a two-fold dilution of the patient's serum and then performing the test on each serum dilution. This same quantative (titration) procedure is performed using the specific sensitized matrix by using the serum dilution as indicated in the preceding example. In this case, the positive reaction (titer) would be the reciprocal of the highest serum dilution giving a positive reaction when a two-fold dilution of a patient's serum was used, i.e., if the last tube shows a positive reaction, the tube containing a 1:128 dilution of the patient's serum, then the titer would be 128.

EXAMPLE 8.

In this example, a spectrophotometer procedure was utilized. There was very little difference in the operation of this diagnostic test procedure from Example 6, except that the reaction was carried out in a cuvette designed for a specific spectrophotometer, i.e., a Beckman DU spectrophotometer. In this procedure, the instrument was set at 470 nM (absorption maximum curve for quaiacol) and blanked against the negative control. The only procedural difference was that with the delta OD procedure, the tubes are inverted several times and immediately placed in a spectrophotometer. The delta OD is read for approximately 3 minutes and the average delta OD per minute was calculated. The only necessary precaution in this procedure is that the specific sensitized matrix must not be trapped in the cuvettes so as to not obstruct the path of light going through the cuvette. A positive reaction would be one in which there was a delta OD of 0.010 units or greater. Several positive reactions were obtained having a delta OD of 0.023, 0.067, 0.076, 0.130 and 0.173, having peroxidase concentrations of 18 ng., 36 ng., 77 ng., 154 ng., 231 ng., respectively. A sample standard curve was then prepared plotting delta OD versus concentration for the full 10minute period, however delta OD was calculated for 3 minutes. Note that the sensitivity for this type of readout is in the lower nanogram range, i.e., less than 18 nanograms. The sensitivity of the test was increased approximately ten-fold and quantative results were obtained.

EXAMPLE 9.

In this example, the test procedure was the same as in the delta OD procedure except that only one reading was made on each tube, which was at the 5-minute interval, since from an examination of the OD curves obtained in the previous example, not shown, it can be seen that the color intensity or maximum adsorbancy was reached in 5 minutes with a fixed substrate concentration. The positive reaction is one in which there was an OD reading in the test greater than in the control tube.

To those versed in the art of immunology, it is evident that this technique can be easily converted to quantitative methodology. For example, an unknown concentration of a specific plasma protein is quantitated by simply running a standard curve using known varying concentrations of the protein in question and simply extrapolating the unknown from the known curve.

EXAMPLE 10.

This example illustrates the use of the sensitized matrix to detect *N. gonorrhea* and the use of several readout systems. Due to the antigenic similarities between the saprophytic and infectious strains of neisseria, it has been difficult to prepare an antigen that was specific for infection caused by *N. gonorrhea*. With the discovery that the pili producing strain of *N. gonorrhea* were the only strains that produced infection, it now becomes feasible to produce a serological test for gonorrheae.

The pili can be produced by two different methods, namely:
1. Buchanan, T. M., et al, 1973. Quanitative determination of Antibody to Gonococcal Pili: Changes in antibody levels with Gonococcal infections. J. Clin. Invest. Vol. 52: 2896–2909.
2. Punsalang, A. P. and W. D. Sawyer: 1973. Role of Pili in the Virulence of Neisseria Gonorrheae. Infection and Immunity 8:255–263.

In general, pili are grown in a liquid medium (Buchanan's method) and separated by high speed centrifugation in a Sharpless centrifuge. The resultant liquid is precipitated by changing the pH to 4.0. The precipitate is resuspended in a buffer and further purified by alternate dialysis and precipitation with 0.1 M MgCl.

In the Punsalang and Sawyer method, N. gonorrhea is grown on a solid medium, and the pili are removed from the bacteria by subjecting them to the action of a Waring blender. The pili are precipitated at pH 4 and then further purified by alternate dialysis and precipitation with 0.1 M MgCl.

In this example, the matrices were sensitized by the substitution of 0.05 to 0.1 ml. of the purified pili preparation for the E. histolytica antigen. From this point on, the matrices were treated the same as in Example 1. The matrices then were ready to be used in the diagnostic test for gonorrheae. The diagnostic test procedure was performed as outlined in Example 6.

However, after the sensitized matrix has been subjected to incubation with a patient's blood serum suspected of having antibodies to N. gonorrhea, the matrix can be incubated with several different labeled antibodies depending on the readout system desired.

When the labeled antibody used is labeled with the enzyme peroxidase, the final reaction can be visualized by incubation with the quaiacol mixture as outlined in Example 6, or it can be incubated with the substrate mixture described in Table II giving an emerald green color or a lavender color when incubated with the substrate mixture described in Table III. These reactions can also be read using a spectrophotometer as described under Specific Sensitized Matrix Diagnostic Tests.

In using the fluorescent readout system, the matrix was incubated with the patient's blood serum and then subjected to the indicator which is a FITC labeled antibody. After incubation and appropriate washing, the reaction was read by exposing the matrix to an ultraviolet lamp such as a Wood's lamp. The fluorescence is read visually. Alternatively, the reaction can be read by a fluorometer such as a Turner fluorometer or an Aminco Microspectrophotofluorometer.

In using the radioisotope readout system, the procedures are identical to the enzyme tagged and fluorescent systems described above except that the indicator antibody was a IgG-I[131] or IgG-I[125] labeled goat anti-human IgG. The amount of antibody bound was determined by counting the isotopes bound onto the matrix by a scintillation counter.

With the fluorescent and radioisotope systems, no additional reactants are necessary, for example the substrate mixture used in the enzyme tagged system.

EXAMPLE 11.

The purpose of this experiment was to compare the relative sensitivites of the sensitized matrix system with the latex particle agglutination technique.

In this example, the latex was Lytron RX-1259, Lot No. 5109, Monsanto Company — (0.5µ size). The latex was sensitized by the addition of 1.0 mg/ml. human IgG per ml. of a 1:100 dilution of latex. All materials were made up in glycine-saline buffer 0.1 M, pH 8.2 The latex-IgG mixture was incubated at 37° C. for 2 hours, centrifuged for 10 minutes at 10,000g and resuspended in fresh GSB. The latex suspension was then washed three times and resuspended in GSB. This is normal practice.

The sensitized matrices were prepared according to Example 1 using 200 ug human IgG matrices which were first attached to the bottom of polystyrene plastic tubes and sensitized in situ.

The reaction mixture was prepared according to Example 1 with one modification. The hydrogen peroxide concentration was reduced from 0.3% to 0.06%. Antibody dilutions were made by two-fold serial dilution of goat anti-human IgG serum in GSB.

One drop (approximately 0.05 ml.) of sensitized latex and one drop (approximately 0.05 ml.) antibody or its dilution was placed on a glass slide, mixed with an applicator stick and rotated for two minutes. The reactions were read and graded placing the glass slide under a fluorescence reading lamp. Reactions were read as either 0 (negative) or 1+, 2+, 3+ or 4+ (positive). A normal goat serum was used as a negative control.

A series of plastic tubes containing the human IgG sensitized matrices were labeled and 0.75 ml. of phosphate buffer 0.1M pH 7.4 was added to each tube. Into Tube No. 1 was placed 0.25 ml. of normal goat serum (NGS) and into each of the remaining tubes was added 0.25 of the appropriate antibody or its dilution. For example, into Tube No. 2 was placed 0.25 ml. of undiluted antibody and into Tube No. 3 was placed 0.25 ml. of the 1:2 dilution. The tubes were shaken to mix the reagents and allowed to incubate at 37° C. for 30 minutes.

After incubation, the reaction mixture was decanted and each tube filled with phosphate buffer, 0.1M, pH 7.4 (15 ml.). The buffer was decanted and the procedure repeated three more times. To each tube was added 1.0 ml. phosphate buffer and 0.1 ml. Of the peroxidase labeled rabbit anti-goat serum (Bioware, Inc. Lot No. 22920674, diluted 1:20 with phosphate buffer, 0.1M pH 7.4). The tubes were shaken to mix the reagents and allowed to incubate at 37° C. for 30 minutes.

After incubation, the reaction mixture was decanted and each tube filled with phosphate buffer. The buffer was decanted and the procedure repeated three more times.

The tubes and the reaction mixture were brought to 37° C. by placing in a water bath and 1.0 ml. of the reaction mixture was placed in each tube. Reactions were read at 5 minutes.

The goat anti-human IgG antiserum (X-IgG) reacted with the latex reagent at dilutions of 1:64 and 1:128. Whereas the same serums reacted in the matrix at dilutions of 1:16,384 and 1:32,768.

The antibody potency of the two antiserums is not known. However, assuming an antibody potency of 2.0 mg/ml., the two antiserums reacted with the latex reagent at a concentration of 7.6 and 3.9 ug. The concentration which reacted with the sensitized matrices was 0.03 and 0.015 ug. This gives an increase in sensitivity of approximately 250 times that of the latex particle agglutination technique.

EXAMPLE 12.

In this example, matrices are prepared as in EXample 1 except that other of the matrix materials disclosed supra are used, and one or more (as in Example 4) of other of the coupling agents are used in the range, all as set forth supra. The specific antigens and antibodies with which the matrices are sensitized include those set forth on Table I, supra. The matrices can be free in the tube as in Example 1, fastened to the tube as in Example 2, or fastened to a stick or rod as in Example 3.

Also, any of the indicator and readout systems can be used, such as indicated in Example 10, and good diagnostic results obtained.

The sensitized matrix can be used for diagnosis of a specific disease or disease state in animals, as well as in man, by incubating blood serum of the animal, instead of man, with a sensitized matrix having antigens or antibodies known to be specific to the disease or disease state coupled together and to the protein carrier molecules of the sensitized matrix. Other than the substitution of blood serum of animals for that of man, the preparation of the sensitized matrix and the methods of diagnosing disease and disease states in aniamls is the same as previously described for man and as illustrated in the foregoing examples.

The present invention therefore is well suited and adapted to attain the objects and ends and has the advantages and features mentioned as well as others inherent therein.

While presently preferred embodiments of the invention have been given for the purpose of disclosure, changes may be made which are within the spirit of the invention as defined by the scope of the appended claims.

What is claimed is:

1. A specific sensitized matrix for diagnosing disease comprising,
   an insoluble, inert matrix having a network of pores,
   carrier protein molecules,
   a specific immunological reactant selected from the group consisting of antigens and antibodies, and
   a coupling agent coupling the carrier protein molecules together, and coupling the specific immunological reactant to the carrier protein molecules and forming a network of the carrier protein molecules, the immunological reactant and the coupling agent,
   the last-mentioned network being immobilized within the network of pores of the matrix.

2. The specific sensitized matrix of claim 1 where the matrix is polyurethane foam having at least 50% by volume open pores.

3. The specific sensitized matrix of claim 1 in which the coupling agent is glutaraldehyde in which residual reactive aldehyde groups are blocked by combination with amino groups.

4. The specific sensitized matrix of claim 3 where the amino groups are from glycine.

5. The specific sensitized matrix of claim 1 where the specific immunological reactant is derived from an infectious disease.

6. The specific sensitized matrix of claim 1 where the specific immunological reactant is gonococcus pili.

7. The specific sensitized matrix of claim 1 where the specific immunological reactant is an allergen extract.

8. The specific sensitized matrix of claim 1 where the specific immunological reactant is derived from a disease state.

9. A method of preparing a specific sensitized matrix for diagnosing disease comprising,
   saturating at least a portion of an insoluble matrix having a network of pores with a buffered mixture having a pH of from about 4 to about 7, the buffered mixture comprising,
   protein carrier molecules,
   a specific immunological reactant selected from the group consisting of antigens and antibodies, and
   a coupling agent capable of bonding the protein carrier molecules together and of bonding the specific immunological reactant to the protein carrier molecules,
   incubating the saturated matrix so as to couple the protein carrier molecules and the specific immunological reactant together in a network immobilized in the network of pores of the matrix, and
   washing the matrix of unreacted components of the mixture.

10. The method of claim 9 where,
    the coupling agent is glutaraldehyde, and
    after washing, residual reactive aldehyde groups are blocked by combining them with amino groups from an amino acid,
    then washing the matrix of uncombined components of the amino acid.

11. The method of claim 10 where
    the amino acid is glycine.

12. The method of claim 9 where
    the matrix is polyurethane foam,
    the coupling agent is glutaraldehyde, and
    after washing, residual reactive aldehyde groups are blocked by combining them with amino groups from glycine,
    then washing the matrix of uncombined components of the glycine.

13. The method of claim 9 where
    the mixture is buffered with an acetate buffer solution having a pH of about 4.9.
    the coupling agent is a solution of glutaraldehyde and incubation is at about 4° C. for a period of about 2 to 24 hours.

14. The method of claim 9 where
    the specific immunological reactant is derived from an infectious disease.

15. The method of claim 9 where
    the specific immunological reactant is gonococcus pili.

16. The method of claim 13 where
    the specific immunological reactant is an allergen extract.

17. The method of claim 13 where
    the specific immunological reactant is derived from a disease state.

18. A method of diagnosis of a specific disease comprising,
    incubating blood serum of a patient being tested for the specific disease with a sensitized matrix comprised of an insoluble, inert matrix having a network of pores and a network of protein carrier molecules and immunological reactant selected from the group consisting of antigens and antibodies and known to be specific to the disease coupled together by a coupling agent and immobilized within the network of pores,
    so as to bind the patient's blood serum to the sensitized matrix,
    washing the matrix of any unbound serum,
    then contacting the sensitized matrix with a reagent capable of catalyzing a measurable reaction, whereby said reagent is bound to any corresponding opposite reactant of the immunological reactant selected, washing any unbound reagent from the sensitized matrix, and then, subjecting the sensitized matrix to a suitable substrate thereby producing a measurable catalytic reaction for measurement of the reagent.

19. A method of preparing a specific sensitized matrix for diagnosing disease comprising, saturating at least a portion of an insoluble matrix having a network of pores with a buffered mixture having a pH of from about 4 to 7 of protein carrier molecules and a coupling agent capable of bonding the protein carrier molecules together, incubating the saturated matrix so as to polymerize and couple together the protein carrier molecules, washing the matrix of unreacted components of the mixture, then contacting the matrix with a buffered mixture having a pH of from about 4 to 7 with a specific immunological reactant and additional coupling agent capable of bonding the specific immunological reactant to the protein carrier molecules polymerized in the matrix, then incubating the matrix so as to couple the specific immunological reactant to the protein carrier molecules, and then washing the matrix of unreacted components.

20. The method of claim 19 where the reactant is an enzyme labeled anti-human IgG serum.

21. The method of claim 19 where the reactant capable of catalyzing a measurable reaction is selected from the group consisting of anti-human IgG and IgG/IgM-peroxidase labeled serum.

22. The method of claim 21 where the measurable reaction is achieved by reacting the peroxidase, and the substrate is guaiacol in the presence of hydrogen peroxide.

23. A method of diagnosis of a specific disease comprising, incubating blood serum of a patient being tested for the specific disease with a sensitized matrix comprised of an insoluble, inert matrix having a network of pores and a network of protein carrier molecules and immunological reactant selected from the group consisting of antigens and antibodies and known to be specific to the disease coupled together by a coupling agent and immobilized within the network of pores, so as to bind the patient's blood serum to the sensitized matrix, washing the matrix of any unbound serum, then incubating the sensitized matrix with fluoresceinisothiocyanate labeled anti-human IgG serum.

24. The method of claim 23 including, subjecting the incubated sensitized matrix to a measurement of fluorescence.

25. A method of diagnosis of a specific disease comprising, incubating blood serum of a patient being tested for the specific disease with a sensitized matrix comprised of an insoluble, inert matrix having a network of pores and a network of protein carrier molecules and immunological reactant selected from the group consisting of antigens and antibodies and known to be specific to the disease coupled together by a coupling agent and immobilized within the network of pores, so as to bind the patient's blood serum to the sensitized matrix, washing the matrix of any unbound serum, then incubating the sensitized matrix with an anti-human radioisotope labeled serum, and subjecting the incubated sensitized matrix to a measurement of radioactivity counter capable of measuring any reacted radioisotopes.

* * * * *